US010494410B2

(12) United States Patent
Caboche et al.

(10) Patent No.: US 10,494,410 B2
(45) Date of Patent: Dec. 3, 2019

(54) INHIBITOR PEPTIDES OF ERK-TYPE MAP KINASE

(71) Applicants: Universite Pierre Et Marie Curie, Paris (FR); Centre National de la Recherche Scientifique - CNRS -, Paris (FR)

(72) Inventors: Jocelyne Caboche, Vicq (FR); Peter Vanhoutte, Alfortville (FR)

(73) Assignees: UNIVERSITE PIERRE ET MARIE CURIE, Paris (FR); Centre National de la Recherche Scientifique—CNRS—, Paris (FR)

( * ) Notice: Subject to any disclaimer, the term of this patent is extended or adjusted under 35 U.S.C. 154(b) by 113 days.

(21) Appl. No.: 15/049,825

(22) Filed: Feb. 22, 2016

(65) Prior Publication Data
US 2016/0244493 A1 Aug. 25, 2016

Related U.S. Application Data

(62) Division of application No. 11/815,185, filed as application No. PCT/EP2006/002068 on Feb. 16, 2006, now abandoned.

(30) Foreign Application Priority Data

Feb. 17, 2005 (EP) .................. 052903630

(51) Int. Cl.
C07K 19/00 (2006.01)
C12N 15/62 (2006.01)
C07K 14/47 (2006.01)
C07K 14/82 (2006.01)
A61K 47/62 (2017.01)
A61K 47/64 (2017.01)
A61K 38/00 (2006.01)

(52) U.S. Cl.
CPC .......... C07K 14/4702 (2013.01); A61K 47/62 (2017.08); A61K 47/645 (2017.08); C07K 14/82 (2013.01); A61K 38/00 (2013.01); C07K 2319/09 (2013.01); C07K 2319/095 (2013.01); C07K 2319/10 (2013.01); C07K 2319/70 (2013.01)

(58) Field of Classification Search
None
See application file for complete search history.

(56) References Cited

U.S. PATENT DOCUMENTS 66,385,509 10/2003 Suzawa et al.
7,244,614 B2 7/2007 Chan et al.
2005/0148031 A1 7/2005 Allbritton et al.

FOREIGN PATENT DOCUMENTS

| WO | WO 94/04686 A1 | 3/1994 |
| WO | WO 98/25614 A1 | 8/1998 |
| WO | WO 98/52614 A2 | 11/1998 |
| WO | WO 00/62067 A1 | 10/2000 |
| WO | WO 02/39947 A2 | 5/2002 |
| WO | WO 03/012068 A2 | 2/2003 |
| WO | WO 2004/068139 A2 | 8/2004 |

OTHER PUBLICATIONS

Murphy et al., Molecular interpretation of ERK signal duration by immediate early gene products, Nat. Cell Biol. 4(8): 556-564, 2002.*
Bardwell et al., "Docking sites on mitogen-activated protein kinase (MAPK) kinases, MAPK phosphatases and the Elk-1 transcription factor compete for MAPK binding and are crucial for enzymatic activity", Biochemical Journal, Mar. 15, 2003, vol. 370, No. 3, pp. 1077-1085, XP002366352.
Hancock et al., "Identification of Novel Extracellular Signal-Regulated Kinase Docking Domain Inhibitors", Journal of Medicinal Chemistry, Jun. 21, 2005, 48, 4586-4595.
Bonny et al., "Cell-Permeable Peptide Inhibitors of JNK: Novel Blockers of Beta-Cell Death", Diabetes, Jan. 2001, vol. 50, No. 1, pp. 77-82, New York, NY.
Borsello et al., "A peptide inhibitor of c-Jun N-terminal kinase protects against exitotoxicity and cerebral ischemla", Nature Medicine, Aug. 24, 2003, 9(9). pp. 1180-1186.
Pouyssegur et al., "Fidelity and spatio-temporal control in MAP kinase (ERKs) signalling", Biochemical Pharmacology, Sep. 1, 2002, vol. 64, No. 5-6, pp. 755-763.
Jacobs et al., "Multiple docking sites on substrate proteins form a modular system that mediates recognition by ERK MAP kinase", Genes & Development, 1999, 13, pp. 163-175.
Fischer et al., "Structure-Activity Relationship of Truncated and Substituted Analogues of the Intracellular Delivery Vector Penetratin", Journal of Peptide Research, vol. 55, No. 2, pp. 163-172, XP000899124, Feb. 2000.
Mann et al., "Endocytosis and Targeting of Exogenous HIV-1 Tat Protein", The Embo Journal, vol. 10, No. 7, pp. 1733-1739, XP001205687 (1991).
Schwarze et al., "In Vivo Protein Transduction: Delivery of a Biologically Active Protein into the Mouse", Science, American Association for the Advancement of Science, vol. 285, No. 5433, pp. 1569-1572, XP002140133 (Sep. 3, 1999).
Nori et al., "Tat-Conjugated Synthetic Macromolecules Facilitate Cytoplasmic Drug Delivery to Human Ovarian Carcinoma Cells", Bioconjugate Chemistry, vol. 14, No. 1, pp. 44-50, XP002347558 (2003).
Watanabe et al., "Bio-effectiveness of Tat-catalase conjugate: a potential tool for the identification of H2O2-dependent cellular signal transduction pathways", Biochemical and Biophysical Research Communications, vol. 303, No. 1, pp. 287-293, XP002366348 (Mar. 28, 2003).
Hall et al., "Transduction of a dominant-negative H-Ras into human eosinophils attenuates extracellular signal-regulated kinase activation and interleukin-5-mediated cell viability", Blood, vol. 98, No. 7, pp. 2014-2021, XP002366349 (Oct. 1, 2001).

(Continued)

Primary Examiner — Claire Kaufman
(74) Attorney, Agent, or Firm — Miller, Matthias & Hull LLP

(57) ABSTRACT

The invention concerns peptides useful as MAP kinase/ERK pathway-specific inhibitors relative to a given substrate in a given subcellular compartment.

7 Claims, 7 Drawing Sheets

Specification includes a Sequence Listing.

(56) References Cited

OTHER PUBLICATIONS

Myou et al., "Blockade of Focal Clustering and Active Conformation in Beta 2-Integrin-Mediated Adhesion of Eosinophils to Intercellular Adhesion Molecule-1 Caused by Transduction of HIV TAT-Dominant Negative Ras",The Journal of Immunology, vol. 169, No. 5, pp. 2670-2676, XP002366350 (Sep. 1, 2002).

Rao et al., "elk, Tissue-Specific ets-Related Genes on Chromosomes X and 14 near Translocation Breakpoints", Science, vol. 244, pp. 66-70 (Apr. 7, 1989).

\* cited by examiner

Western-Blot P-ERK1/2

Immunoprecipitations

Western-Blot P-Elk-1

Immunofluorescence P-ERK

Immunofluorescence P-MSK-1

Biochemical effects of the peptide P2 on neurons *in vitro*

Intracerebral injection of the peptide F2 according to the invention

Section of striatum of mouse having received
cocaine side microinjected with a saline solution P-ERK  P-Elk-1

Section of striatum of mouse having received
cocaine side microinjected with the peptide P2 (0.5µl)

P-ERK  P-Elk-1

Effect of the peptide P2 on neurons *in vivo*

INHIBITOR PEPTIDES OF ERK-TYPE MAP KINASE

CROSS REFERENCE TO RELATED APPLICATION

This is a divisional application under 35 U.S.C, § 121 claiming priority to U.S. patent application Ser. No. 11/815,185 filed on Jul. 31, 2007, which is a U.S. National Phase of International Application No. PCT/EP2006/002068 filed 16 Feb. 2006, which claims priority to European Patent Application No. EP 052903630 filed on 17 Feb. 2005, the entire disclosures of which are incorporated herein by reference.

FIELD OF THE DISCLOSURE

The present invention relates to peptides for the selective inhibition of the ERK-type MAP kinase pathway relative to a given substrate and in a given cell compartment.

BACKGROUND OF THE DISCLOSURE

MAP kinases (mitogen activated protein kinases) are ubiquitous proteins involved in varied cell functions.

These proteins ensure intracellular signal transduction: from the surface of the cell to the nucleus. Three major families of MAP kinases (ERK, p38, JNK) have been identified, which correspond to cascade signaling pathways. These signaling pathways play important roles in cell functions: from apoptosis to proliferation, differentiation, or even neuronal plasticity. These functions depend strictly on, firstly, the type of MAP kinase and, for each type of MAP kinase, on its cellular localization.

In order to elucidate the molecular mechanisms governed by ERK signaling pathways and to be able to interfere with this signaling cascade at a given level, it is useful to have specific inhibitors. The compounds currently available: PD98059 (2'-amino-3'-methoxyflavone, a nitrogenous polycyclic inhibitor) and U0126 (1,4-diamino-2,3-dicyano-1,4-bis(2-aminophenyl-thio)butadiene), are inhibitors specific for MEKs, the kinases upstream of ERKs. However, their action is located upstream of ERKs, thereby resulting in complete inhibition of the activation of the latter and, consequently, of all the downstream substrates, without discrimination among them and without distinction with respect to their cellular localization.

It would therefore be useful to have inhibitors which are highly selective for ERKs and which act downstream, on one or more specific substrate(s) that is (are) cytoplasmic or nuclear, in order to minimize, preferably completely avoid, any related, or even pleiotropic, effect.

SUMMARY OF THE DISCLOSURE

The present invention provides peptides which are useful as highly selective inhibitors of ERK-type MAP kinases with respect to their nuclear or cytoplasmic substrates.

According to the present invention, the term "ERK-type MAP kinase" or "ERK" denotes any ERK MAP kinase. In particular, said ERK-type MAP kinase can be a mammalian, in particular human, primate or murine, MAP kinase. It can also be non-mammalian (lamprey, zebrafish, *C. elegans, drosophila, xenopus*). According to the present invention, the term "ERK inhibitor" or "ERK-type MAP kinase inhibitor" denotes any compound which makes it possible to inhibit the kinase function of ERK on at least one given substrate.

According to the present invention, the term "peptide" or "peptide chain" denotes any chain of amino acids. Said chain of amino acids generally contains from 2 to 100 residues, preferably from 5 to 75 residues, more preferably from 10 to 50 residues (see IUPAC definition).

Preferably, said chain contains 2, 3, 4, 5, 6, 7, 8, 9, 10, 11, 12, 13, 14, 15, 16, 17, 18, 19, 20, . . . , 50, . . . , 100 amino acid residues.

According to the present invention, the term "amino acid" or "amino acid residue" denotes any amino acid residue known to those skilled in the art (see, for example: N. Sewald, H.-D. Jakubke, Peptides: Chemistry and Biology 2002, Wiley-VCH Verlag GmbH, Weinheim; IUPAC nomenclature).

This comprises the natural amino acids (including, for example, according to the three-letter code, Ala, bAla, Arg, Asn, Asp, Cys, Gln, Glu, Gly, His, Ile, Leu, Lys, Met, Phe, Pro, Ser, Thr, Trp, Tyr, Val), and also rare and/or synthetic amino acids and their derivatives (including, for example, Aad, Abu, Acp, Ahe, Aib, Apm, Dbu, Des, Dpm, Hyl, MeLys, MeVal, Nva, HAO, NCap, Abu, Aib, MeXaa and the like (see, for example: J. S. Nowick, J. O. Brower, J. Am. Chem. Soc. 2003, 125, 876-877; R. Aurora, G. D. Rose, Protein Science 1998, 7, 21-38; W. Maison, E. Arce, P. Renold, R. J. Kennedy, D. S. Kemp, J. Am. Chem. Soc. 2001, 123, 10245-10254; D. Obrecht, M. Altorfer, J. A. Robinson, Adv. Med. Chem. 1999, 4, 1-68; K. Muller, D. Obrecht, A. Knierzinger, C. Stankovic, C. Spiegler, W. Bannwarth, A. Trzeciak, G. Englert, A. M. Labhard, P. Schonholzer in Perspectives in Medicinal Chemistry, (Eds.: B. Testa, E. Kyburz, W. Fuhrer, R. Giger), Verlag Hely. Chim. Acta, Basel, 1993, pp. 513-533; F. Formaggio, A. Bettio, V. Moretto, M. Crisma, C. Toniolo, Q. B. Broxterman, J. Peptide Sci. 2003, 9, 461-466).

Said amino acid residue or its derivative can be any isomer thereof, in particular any chiral isomer, for example the L- or D-isoform, and mixtures thereof. The D-isoform has the advantage of better stability.

The term "amino acid derivative" here denotes any amino acid derivative, in particular any derivative known to those skilled in the art (see, for example: N. Sewald, H.-D. Jakubke, Peptides: Chemistry and Biology 2002, Wiley-VCH Verlag GmbH, Weinheim: IUPAC nomenclature).

For example, the amino acid derivatives include residues that can be derived from natural amino acids bearing additional side chains, for example alkyl side chains, and/or substitutions of heteroatoms.

The notion of an "amino acid sequence" is known to those skilled in the art. An amino acid sequence comprises at least two residues covalently bound by means of at least one peptide bond.

The amino acid sequences will subsequently be given using the one-letter code.

Said peptide can be obtained by methods known to those skilled in the art, for example said peptide can be obtained by synthetic methods, such as solid-support synthesis or synthesis in solution (synthetic peptides), or techniques derived from molecular biology (recombinant peptide).

DETAILED DESCRIPTION OF THE DISCLOSURE

Figure 1:
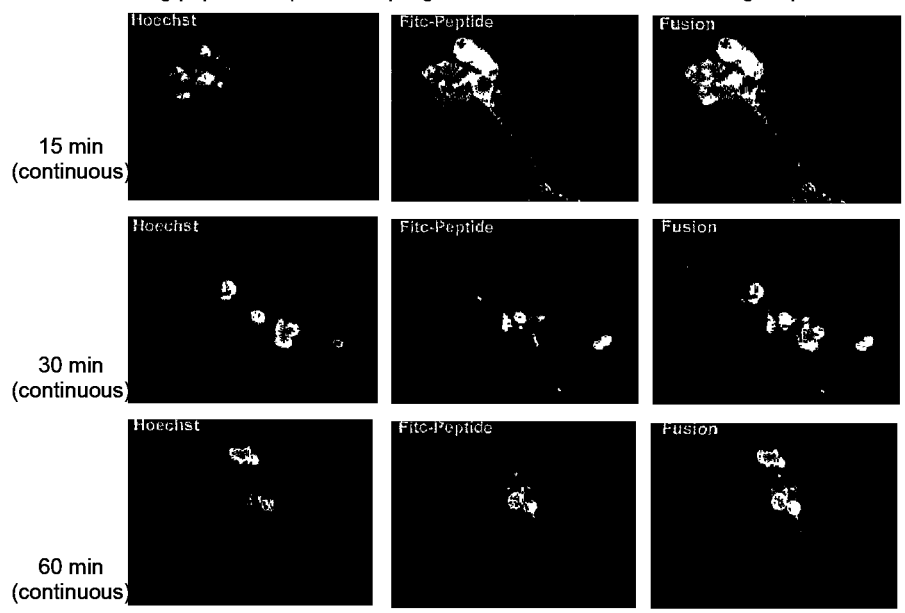
FIG. 1 shows results obtained for a 100 μM concentration of a peptide F2, as a function of time.

The present invention relates to a peptide comprising:
- at least one amino acid sequence which allows said peptide to penetrate into a cell;
- an intracellular targeting amino acid sequence chosen from NESs;
- optionally, an intracellular targeting sequence chosen from NLSs;
- an amino acid sequence corresponding to a docking domain sequence of a substrate of an ERK-type MAP kinase;
- optionally, at least one "spacer" sequence;
- optionally, an enzymatic cleavage sequence possibly surrounded by spacer sequences.

The expression "amino acid sequence which allows said peptide to penetrate into a cell" denotes, according to the present invention, any amino acid sequence that facilitates and/or mediates the transport of said peptide from the outside of a cell to its inside. Such sequences are known to those skilled in the art. Said sequence which allows said peptide to penetrate into a cell can be chosen according to the cell type of said cell, in order to optimize the penetration efficiency.

According to one embodiment, said sequence which allows said peptide to penetrate into a cell is from 2 to 20 residues in length, in particular 6, 7, 8, 9, . . . , 17, 18, 19 or 20 residues.

According to one embodiment, said sequence which allows said peptide to penetrate into a cell is chosen from: the sequence of the HIV-TAT penetrating peptide, penetratin, a sequence of seven to eleven arginines, a sequence referred to as "X7/11R sequence".

According to one embodiment, said sequence which allows said peptide to penetrate into a cell is chosen from sequences derived from the Vectocell® family (or diatos peptide vectors: DPVs), such as the penetration sequences described in De Coupade et al., Biochem. J. (2005) 390, 407-418 and WO 01/64738.

The term "X7/11R sequence" is intended to mean any peptide sequence of 7 to 25, preferably 7 to 20 amino acids containing between seven and eleven arginine residues (7/11R), in which the arginine residues (R) can be placed randomly within said sequence. Examples are given below, but those skilled in the art are able to give other possibilities.

According to one embodiment, said sequence which allows said peptide to penetrate into a cell is chosen from:

| SEQ ID No. | Sequence of penetration | Origin |
|---|---|---|
| 1 | GRKKRRQRRR | HIV-TAT |
| 2 | RQIKIWFQNRRMKWKK | Penetratin |
| 3 | RRRRRRR | 7R |
| 4 | XRRRRRRRX | X7R (example) |
| 5 | XRRRXRRRR | X7R (other example) |
| 6 | RRRXRRRRX | X7R (other example) |
| 7 | RRRRRRRXX | X7R (other example) |
| 8 | XXRRRRRRR | X7R (other example) |
| 9 | RRRRRRRRRRR | 11R |
| 10 | XRRRRRXRRRRR | X11R (other example) |
| 11 | RRRRRXRRRRRX | X11R (other example) |
| 48 | GAYDLRRRERQSRLRRRERQSR | DPV15b(*) |
| 49 | SRRARRSPRHLGSG | DPV10(*) |
| 50 | LRRERQSRLRRERQSR | DPV15(*) |
| 51 | VKRGLKLRHVRPRVTRMDV | DPV1047(*) |
| 52 | RKKRRRESRKKRRRES | DPV3(*) |

(*) De Coupade et al., Biochem. J. (2005) 390, 407-418 and WO 01/64738.

The notion of NLS (nuclear localization signal) is known to those skilled in the art. It is generally an amino acid sequence which allows the targeting of a given protein to the nucleus, via the phenomenon of nuclear import.

According to one embodiment, said NLS sequence is a sequence rich in basic amino acids (arginine or lysine).

According to one embodiment, said NLS sequence is from 2 to 20 residues in length, in particular 6, 7, 8, 9, . . . , 17, 18, 19 or 20 residues.

According to one embodiment, said NLS sequence is chosen from:

| SEQ ID No. | NLS sequence | Origin |
|---|---|---|
| 12 | PKKKRKV | SV40 large T-antigen |
| 13 | KRPAAIKKAGQAKKKK | nucleoplasmin |
| 14 | RQARRNRRRRWR | HIV1Rev |
| 1 | GRKKRRQRRR | HIV-TAT |
| 2 | RQIKIWFQNRRMKWKK | penetratin |
| 3 | RRRRRRR | 7R |
| 9 | RRRRRRRRRRR | 11R |

The notion of NES (nuclear export signal) is known to those skilled in the art. They are generally amino acid sequences which mediate nuclear export, resulting in translocation of a given protein from the nucleus to the cytoplasm.

According to one embodiment, said NES sequence is from 2 to 20 residues in length, in particular 6, 7, 8, 9, . . . , 10, 11, 12, . . . , 17, 18, 19 or 20 residues.

According to one embodiment, said NES sequence is chosen from:

| SEQ ID No. | NES sequence | Origin |
|---|---|---|
| 15 | XLXXXLXXLXLX | Elk-1 type consensus |
| 16 | XLXXXLXXLXRX | Net type consensus |
| 17 | ALQKKLEELELD | MAPKK |
| 18 | TLWQFLLQLLLD | Net (ERK substrate) |
| 19 | TLWQFLLQLLRE | Elk-1 (ERK substrate) |

Said amino acid sequence corresponding to a docking domain sequence of a substrate of an ERK-type MAP kinase can comprise any docking domain of an ERK substrate known to those skilled in the art.

The notion of "docking domain" is known to those skilled in the art. It is generally a portion of the substrate of a MAP kinase which specifically conditions the interaction and/or the recruitment between said substrate and said MAP kinase. It is all or part of a docking site of said substrate for said MAP kinase. The sequence of said docking domain is therefore specific and selective for a given interaction.

Thus, advantageously according to the invention, each of these docking domain sequences corresponds to a portion (amino acid sequences) of an ERK MAP kinase substrate, which portion specifically conditions the interaction and/or the recruitment between said substrate and said ERK-type MAP kinase.

According to one embodiment, said amino acid sequence corresponding to a docking domain sequence of a substrate of an ERK-type MAP kinase can comprise only a part of a docking domain of an ERK substrate. Thus, since said amino acid sequence corresponding to a docking domain sequence of a substrate of an ERK-type MAP kinase contains only a portion of the docking domain, it is possible to obtain inhibition of several given substrates of ERK.

According to one embodiment of the present invention, said amino acid sequence corresponding to a docking domain sequence of a substrate of an ERK-type MAP kinase is 12-25 residues in length, preferably 13, 14, 15, 16, 17, 18, 19, 20, 21, 22, 23 or 24 residues.

According to one embodiment, said docking domain sequence is chosen from FXFP-type docking domain sequences and D-type docking domain sequences.

According to one embodiment, said docking domain sequence is 12-25 residues in length, preferably 13, 14, 15, 16, 17, 18, 19, 20, 21, 22, 23 or 24 residues.

Optionally, according to one embodiment, said sequence may be reduced so as to correspond to the minimum FXFP-type sequence. Thus, according to one embodiment, said docking domain sequence can be 3-11 residues in length, for example, 3, 4, 5, 6, 7, 8, 9, 10 or 11 residues.

The term "D-type docking domain" sequence is here intended to mean any D-type docking domain sequence known to those skilled in the art. This includes in particular sequences of hydrophobic amino acids followed by a sequence of basic amino acids; sequences of hydrophobic amino acids followed by a sequence of basic amino acids and by a "leucine X leucine" (LXL) sequence; sequences of basic amino acids followed by the "leucine X leucine" sequence and then by a sequence of hydrophobic amino acids.

The expression "FXFP-type docking domain sequence" is here intended to mean any FXFP-type docking domain sequences known to those skilled in the art. This includes in particular the sequences of the "FXFP" domains and the corresponding flanking Nter and Cter sequences of said substrate). This also includes docking domains of type (F/Y)X(F/Y)P, i.e. of type:
FXFP, or
FXYP, or
YXFP, or
YXYP,
where F denotes phenylalanine (Phe), X denotes any amino acid (Xaa), Y denotes tyrosine and P denotes proline (Pro).

According to one embodiment, said docking domain sequence is chosen from:

| SEQ ID No. | Docking domain sequence | Type of the docking domain | Substrate of ERK |
|---|---|---|---|
| 20 | SPAKLSFQFPSGSAQVHI | FXFP | Elk-1 |
| 21 | SPARLQGANTLFQFPSVLN | FXFP | Sap-1 |
| 22 | SPARLQGPSTLFQFPTLLN | FXFP | Sap-2 |
| 23 | MAVLDRGTSTTTVFNFPV | FXFP | MKP-1 |
| 24 | PNPSPGQRDSRFSFPD | FXFP | KSR |
| 25 | SLTPTAAHSGSHLFGFPP | FXFP | GATA-2 |
| 26 | KGRKPRDLELPLSPSLL | D | Elk-1 |
| 27 | RSKKPKGLGLAPTLVI | D | Sap-1 |
| 28 | KAKKPKGLEISAPPLLVL | D | Sap-2 |
| 29 | SSILAQRRVRKLPSTTL | D | Rsk-1 |
| 30 | RRSTLAQRRGIKKITSTAL | D | Rsk-2 |
| 31 | SSNLAQRRGMKRLTSTRL | D | Rsk-3 |
| 32 | KSRLARRRALAQAGRSRD | D | Mnk-1 |
| 33 | QSKLAQRRQRASLSSATPV | D | Mnk-2 |
| 34 | KAPLAKRRKMKKTSTSTE | D | Msk-1 |
| 35 | RFSTIVRRRAKGAKGAG | D | MKP-1 |
| 36 | PGIMLRRLQKGNLPVRAL | D | MKP-3 |
| 37 | LPALLLRRLRRGSLSVR | D | MKP-4 |
| 38 | GLQERRGSNVSLTLDM | D | STEP |
| 42 | LVTTTPTSTQFLYPKVAA | FXFP | JunD |
| 43 | CTTYTSSFVFTYPEEADSFPS | FXFP | c-Fos |
| 44 | SNGVITTTPTPPGQYFYPRG | FXFP | JunB |
| 45 | MLKKDALTLSLAEQGAA | D | JunD |
| 46 | SGAALCALGKECFLELAPDF | D | Ets-1 |
| 47 | NGQMLCMLGKERFLELAPDF | D | Ets-2 |

A single substrate can sometimes contain several docking domains for ERK. This is the case, for example, of Elk-1 and MKP-1 with respect to ERK. In this case, one or other of the docking domain sequences may be used in a peptide according to the invention for blocking the ERK/substrate interaction. Alternatively, the joint use of two peptides according to the invention, one of the peptides containing a docking domain sequence, for example an FXFP sequence, and the other peptide containing another docking domain sequence, for example a D sequence, will make it possible to improve the inhibition at subliminal concentrations.

Advantageously according to the invention, said peptide has the following properties: once brought into contact with a cell, by virtue of said amino acid sequence which allows said peptide to penetrate into a cell, the peptide according to the invention enters said cell. Subsequently, depending on the nature of said intracellular targeting sequence, said peptide becomes localized either in the nucleus (if NLS) or in the cytoplasm (if NES). Alternatively, in the absence of an additional intracellular targeting sequence, given the content rich in basic amino acids of said sequence which allows penetration, the latter also plays the role of an NLS, such that said peptide is localized in the nucleus. Thus, according to the structure of said peptide according to the invention, the latter advantageously adopts a specific intracellular localization. Said docking domain sequence then plays an inhibitory role: it advantageously makes it possible to mimic the presence of said substrate with respect to the ERK-type MAP kinase, thus resulting in a selective and specific inhibition of the interaction between ERK and said substrate, with a specific intracellular localization: depending on the case, the inhibition is specific for the nuclear interaction, or specific for the cytoplasmic interaction, between ERK and said substrate. Thus, advantageously according to the invention, the resulting inhibition is specific not only for the substrate/ERK couple (due to the docking domain), but also specific in terms of the intracellular localization (selective inhibition of the nuclear interaction, or selective inhibition of the cytoplasmic interaction: specific differential inhibition).

Said cell is a eukaryotic cell, preferably a higher eukaryotic cell, for example a mammalian cell or a human cell. It may be a cell undergoing mitosis or a quiescent (post-mitotic) cell, for example a neuronal cell.

Advantageously according to the invention, said optional spacer sequence makes it possible to ensure a certain conformational flexibility between said sequence which allows said peptide to penetrate into a cell and said docking domain sequence. For example, said spacer sequence can comprise at least one, preferably several proline residues, for example 2, 3 or 4 proline residues.

Moreover, according to one embodiment, said peptide can comprise an enzymatic cleavage site for separating said amino acid sequence for penetration of said peptide into a cell, from the rest of said peptide. Advantageously according to the invention, said peptide can thus comprise two consecutive cysteine residues, thus allowing intracellular cleavage by cytoplasmic glutathione (the disulfide bridges that exist between these two residues are cleaved after penetration into the cell). Any other enzymatic cleavage site, in particular for cleavage by an intracellular protease known to those skilled in the art, can also be used. According to one embodiment of the invention, said cleavage site can be a cleavage site for cysteine proteases of caspase type or for NSE (neuron specific enolase).

According to one embodiment, the peptide according to the invention is coupled to at least one fluorophore, preferably covalently. Said fluorophore can be any fluorophore known to those skilled in the art. In particular, said fluorophore can be chosen from Fam, Hex, Tet, Joe, Rox, Tamra, Max, Edans, Cy dyes such as Cy5, Cy2 or Cy3, fluorescein, coumarin, eosin, rhodamine, bodipy, alexa, cascade blue, Yakima yellow, Lucifer yellow and Texas red AMCA (registered trade marks). Alternatively, said peptide can be biotinylated and visualized, indirectly, with avidin labeled with the fluorophores described above. Said peptide may also be coupled to an enzymatic label, for example of beta-galactosidase type. Advantageously according to the invention, said fluorophores, biotin or enzyme (beta-galactosidase, for example) are located at the C-terminal or N-terminal region of the docking site of said peptide so as to be able to locate it in the whole animal in vivo, on a preparation of cells in vitro, as well as on a preparation of fixed cells.

The present invention also relates to a nucleic acid encoding a peptide as described above. For a given peptide, those skilled in the art will be able to identify which nucleic acid sequence(s) encode(s) such a peptide, on the basis of the genetic code, the degeneracy of said code, and codon adaptation according to species.

The present invention also relates to an expression vector comprising a nucleic acid encoding a peptide as described above.

According to one embodiment, said expression vector is a eukaryotic expression vector.

Said expression vector will advantageously be suitable for a given cell type, depending on the use for which the peptide according to the invention is intended. Thus, those skilled in the art will be able to design such as vector. In particular, those skilled in the art will be able to choose between a constitutive or tissue-specific promoter, allowing the expression of said peptide from said vector. In addition, said expression promoter can be chosen from constitutive promoters, inducible promoters and specific promoters, for example tissue-specific promoters.

According to one embodiment, said expression vector contains a nestin-type promoter, in order to allow the early expression of said peptide during development.

According to another embodiment, said expression vector comprises at least one tissue-specific promoter, in order to allow the expression of said peptide in targeted tissues.

Furthermore, for a given tissue, the expression of said peptide may be restricted to certain regions of said tissue, for example certain regions of the brain:

According to one embodiment, said expression vector contains a CaMKII-type promoter, in order to obtain a preferential expression in the hippocampus (site of spatial memory).

According to one embodiment, said expression vector contains a D1-type dopaminergic receptor promoter, in order to obtain a striatum-specific expression (site of addictive processes).

According to one embodiment, said expression vector contains a tyrosine hydroxylase promoter for expression in the substantia nigra compacta (site of degenerative processes in Parkinson's disease).

According to one embodiment, said expression vector also contains an inducible promoter, for example a promoter induced or repressed by tetracycline (Teton, TetOff system).

Said expression vector can contain a bacterial origin of replication which allows its replication in bacterial host cells, typically E. coli.

According to one embodiment, said expression vector is designed so that it can be used to generate transgenic animals, for example transgenic mice, which will express said peptide at desired moments in a given tissue, and, within said tissue (for example in the brain), in a given region.

According to one embodiment, said expression vector is a viral vector. Said viral vector can be chosen from the group of retroviral vectors, canine viral vectors and lentiviral vectors. Said viral vector then allows a tissue-specific expression: a retroviral vector makes it possible to preferentially target dividing cells; a canine virus makes it possible to target post-mitotic cells of neuronal type; a lentiviral vector can integrate into the genome of the host cell without discrimination. Said viral vector can also be used in the context of a gene therapy.

The present invention also relates to a kit containing at least one peptide as described above and/or at least one vector or nucleic acid encoding peptides as described above. In addition, said kit can contain controls (positive or negative) in the form of peptides or of vectors, for carrying out control experiments in parallel with the experiments involving at least one peptide according to the present invention. For example, a negative control peptide can contain a "scrambled" sequence of amino acids. Said kit can, moreover, contain instructions for use.

According to one embodiment, said kit can contain at least two different peptides according to the invention. Said peptides can be intended to inhibit the interaction of an ERK-type MAP kinase with at least two distinct substrates, or just one sole substrate. Indeed, a single substrate can sometimes contain several docking domains for the same MAP kinase. This is the case, for example, of Elk-1 and MKP-1 with respect to ERK. In this case, one or the other of the docking domain sequences may be used in a peptide according to the invention for blocking the ERK/substrate interaction. Alternatively, the joint use of two peptides according to the invention, one of the peptides containing a docking domain sequence, for example an FXFP sequence, and the other peptide containing another docking domain sequence, for example a D sequence, will make it possible to improve the inhibition at subliminal concentrations.

The present invention also relates to the use of a peptide as defined above, as an in vitro or in vivo inhibitor of the activity of said ERK-type MAP kinase relative to a given substrate. This type of use covers very varied fields, depending on the nature of the substrate(s) of said ERK-type MAP kinase, the cell type considered, and the type of extracellular stimulation considered.

Advantageously, said peptide may be labeled, for example coupled to a label (for example fluorophore, biotin or beta-galactosidase), and may thus be tested in vivo in the whole animal after systemic or intratissular injection. After systemic injection, said peptide may be located in the various tissues, including in the central nervous system (the presence of said sequence which allows penetration allowing the blood-brain barrier to be crossed), by virtue of the label coupled to the peptide.

Thus, the peptide according to the invention can be used in the study of various types of phenomena, in particular in neurobiology (study of development, of neuronal plasticity, of addictive processes) and cancerology (cell cycle regulation).

| Extracellular stimulation | Cell type | ERK substrate | Inhibition | Phenomenon |
|---|---|---|---|---|
| Neuro-transmitter | Neuron | Elk-1 MKP-1 | Nuclear | Drug addiction memory learning survival plasticity |
| Neuro-transmitter | Neuron | MKP-3 | Cytoplasmic | Neuro-degeneration, neuronal death, example: Parkinson's |
| Neuro-transmitter | Neuron | Elk-1 | Cytoplasmic | Neuro-degeneration, example: Parkinson's |
| Genetic mutations or stress or cancer or growth factors | Mitotic cells | Elk-1 | Nuclear | Cancer, cell cycle, proliferation, tumor invasion |
| Genetic mutations or stress or cancer or growth factors | Mitotic cells | Ets-1 | Nuclear | Tumor invasion |
| Genetic mutations or stress or cancer or growth factors | Mitotic cells | c-Fos | Nuclear | Tumor progression |

Finally, the present invention relates to a non-human transgenic mammal, in particular a rodent, capable of expressing at least one peptide according to the invention. In particular, said non-human mammal can, for example, be obtained by transgenesis using a vector according to the invention. Those skilled in the art are familiar with transgenesis techniques and will be able to obtain such a mammal using their general knowledge (see, for example, inrp.fr/Access/biotic/biomol/transgen/accueil.htm).

The peptides according to the present invention can have the following structure:

| N-terminal | | | | C-terminal |
|---|---|---|---|---|
| «Penetration sequence» | «C» | «NES targeting» | «docking domain» | |
| «Penetration sequence» | «C» | «docking domain» | «NES targeting» | |
| «Penetration sequence» | «C» | «NES targeting» | «S» | «docking domain» |
| «Penetration sequence» | «S» | «docking domain» | «C» | «NES targeting» |
| «Penetration sequence» | «S» | «docking domain» | | |
| «Penetration sequence» | «S» | «NLS targeting» | «docking domain» | |

-continued

| N-terminal | | | | C-terminal |
|---|---|---|---|---|
| «Penetration sequence» | «S» | «docking domain» | «NLS targeting» | |
| «Penetration sequence» | «S» | «NLS targeting» | «S» | «docking domain» |
| «Penetration sequence» | «S» | «docking domain» | «S» | «NLS targeting» |
| «Penetration sequence» | «O» | «NLS targeting» | «docking domain» | |
| «Penetration sequence» | «O» | «docking domain» | «NLS targeting» | |
| «Penetration sequence» | «O» | «NLS targeting» | «S» | «docking domain» |
| «Penetration sequence» | «O» | «docking domain» | «S» | «NLS targeting» |
| «Penetration sequence» | «O» | «docking domain” | «NES targeting» | |
| «Penetration sequence» | «S» | «docking domain” | «NES targeting» | |
| «Penetration sequence» | «O» | «NES targeting» | «docking domain” | |
| «Penetration sequence» | «S» | «NES targeting» | «docking domain” | |
| «Penetration sequence» | «O» | «docking domain” | «S» | «NES targeting» |
| «Penetration sequence» | «S» | «docking domain” | «S» | «NES targeting» |
| «Penetration sequence» | «O» | «NES targeting» | «S» | «docking domain” |
| «Penetration sequence» | «S» | «NES targeting» | «S» | «docking domain” |
| «Penetration sequence» | «S» | «docking domain» | «NLS targeting» | |
| «Penetration sequence» | «S» | «NLS targeting» | «docking domain» | |
| «Penetration sequence» | «S» | «docking domain» | «S» | «NLS targeting» |
| «Penetration sequence» | «S» | «NLS targeting» | «S» | «docking domain» |
| «Penetration sequence» | «docking domain» | «S» | «NLS targeting» | |
| «Penetration sequence» | «O» | «NLS targeting» | «docking domain» | |
| «Penetration sequence» | «O» | «docking domain» | «NLS targeting» | |
| «Penetration sequence» | «O» | «NLS targeting» | «S» | «docking domain» |
| «Penetration sequence» | «O» | «docking domain» | «S» | «NLS targeting» |
| «docking domain» | «S» | «Penetration sequence» | | |
| or | | | | |
| «docking domain» | «NES targeting» | «O» | «Penetration sequence» | |
| «docking domain» | «NES targeting» | «S» | «Penetration sequence» | |
| «NES targeting» | «docking domain» | «O» | «Penetration sequence» | |
| «NES targeting» | «docking domain» | «S» | «Penetration sequence» | |
| «docking domain» | «S» | «NES targeting» | «O» | «Penetration sequence» |
| «docking domain» | “S” | «NES targeting» | «S» | «Penetration sequence» |
| «docking domain» | «S» | «Penetration sequence» | «O» | «NES targeting» |
| «docking domain» | “S” | «Penetration sequence» | «S» | «NES targeting» |
| «docking domain» | «S» | «Penetration sequence» | | |
| «docking domain» | «NLS targeting» | «S» | «Penetration sequence» | |
| «NLS targeting» | «docking domain» | «S» | «Penetration sequence» | |
| «docking domain» | «S» | «NLS targeting» | «S» | «Penetration sequence» |
| «NLS targeting» | «S» | «docking domain» | «S» | «Penetration sequence» |

-continued

| N-terminal | | | | C-terminal |
|---|---|---|---|---|
| «docking domain» | «NLS targeting» | «O» | «Penetration sequence» | |
| «NLS targeting» | «docking domain» | «O» | «Penetration sequence» | |
| «docking domain» | «S» | «NLS targeting» | «O» | «Penetration sequence» |
| «NLS targeting» | «S» | «docking domain» | «O» | «Penetration sequence» |
| «NES targeting» | «S» | «docking domain» | «O» | «Penetration sequence» |
| «docking domain» | «NLS targeting» | «S» | «Penetration sequence» | |
| «NLS targeting» | «docking domain» | «S» | «Penetration sequence» | |
| «docking domain» | «S» | «NLS targeting» | «S» | «Penetration sequence» |
| «NLS targeting» | «S» | «docking domain» | «S» | «Penetration sequence» |
| «NLS targeting» | «S» | «docking domain» | «Penetration sequence» | |
| «NLS targeting» | «docking domain» | «O» | «Penetration sequence» | |
| «docking domain» | «NLS targeting» | «O» | «Penetration sequence» | |
| «docking domain» | «S» | «NLS targeting» | «O» | «Penetration sequence» |
| «NLS targeting» | «S» | «docking domain» | «O» | «Penetration sequence» |
| «Penetration sequence» | «S» | «docking domain» | | | where:

"penetration sequence" comprises at least one amino acid sequence which allows said peptide to penetrate into a cell;

"S" comprises or corresponds to an optional sequence of spacer type, for example two prolines, or a gamma-aminobutyric acid, which allows flexibility between the penetrating sequence and the docking peptide;

"C" comprises or corresponds to an enzymatic cleavage site which makes it possible to release, inside the cell, the docking peptide and its localization sequence from the penetrating sequence; this cleavage site may or may not comprise a spacer "S", placed in C-term, in N-term or on either side of the cleavage site. In other words, C refers to C on its own, bordered by two S or "flanked" by S on the C-ter or N-ter side;

"targeting" comprises an intracellular targeting sequence of NES or NLS type;

"docking domain" comprises the FXFP-type or D-type docking domain amino acid sequence of a given substrate of ERK.

Advantageously according to the invention, the cleavage site makes it possible to separate the sequence which allows penetration, which is at one of the ends of the peptide, from the rest of the peptide. This is particularly advantageous when the targeting sequence is an NES: the localization of the peptide is then still restricted to the cytoplasm.

The advantages of the peptides according to the invention will be understood more clearly upon reading the following nonlimiting examples.

EXAMPLES

Example 1

Peptides According to the Invention

The following peptides are synthesized by the solid-phase synthesis method: peptides P1, P2 and P3.

Peptides P1 and P2: Inhibition of the Interaction Between Elk-1 and ERK

```
Peptide P1
                                      (SEQ ID No. 39)
GRKKRRQRRRCCTLWQFLLHLLLDSPAKLSFQFPSGSAQVHI
``` in which:
  sequence which allows penetration: GRKKRRQRRR (HIV-TAT penetrating peptide) (SEQ ID No. 1)
  enzymatic cleavage site: CC
  targeting sequence: TLWQFLLHLLLD (NES of Net) (SEQ ID No. 18)
  docking domain sequence: SPAKLSFQFPSGSAQVHI (SEQ ID No. 20)
  P1 penetrates into the cells and becomes localized therein in the cytoplasm.

```
Peptide P2
                                      (SEQ ID No. 40)
GRKKRRQRRRPPSPAKLSFQFPSGSAQVHI
``` in which:

sequence which allows penetration: GRKKRRQRRR (SEQ ID No. 1)

spacer sequence: PP docking domain sequence: SPAKLSFQFPSGSAQVHI (SEQ ID No. 20)

P2 penetrates into the cells and adopts a nuclear localization.

Peptide P3: Inhibition of the Interaction between MKP-3 and ERK

```
Peptide P3 (SEQ ID No. 41)
                                       (SEQ ID No. 41)
GRKKRRQRRRCCTLWQFLLHLLLDPGIMLRRLQKGNLPVRAL
``` in which:

sequence which allows penetration: GRKKRRQRRR (SEQ ID No. 1)

enzymatic cleavage site: CC targeting sequence: TLWQFLLHLLLD (NES of Net) (SEQ ID No. 18)

docking domain sequence: PGIMLRRLQKGNLPVRAL (SEQ ID No. 36)

P3 penetrates into the cells and adopts a cytoplasmic localization.

Example 2

Example of Cell Penetration and of Nuclear Localization of a Peptide According to the Invention The peptide F2 according to the invention ("docking peptide") is used here: it has the same sequence as the peptide P2 (see Example 1), and is coupled to FITC (fluorophore) at its C-terminal end.

It therefore has the following structure:

[HIV-TAT penetrating peptide]-[spacer of PP type]-[FXFP-type docking domain of the ERK/Elk-1 couple]-[FITC].

HEK293 cells are placed in the presence of the peptide F2 at various concentrations (1 mM stock solution in distilled water, then dilutions to 25, 50 and 100 μM in DMEM culture medium), for 15, 30 or 60 minutes, continuously. The cell nuclei are labeled using Hoechst dye (left panel), and the peptide F2 is visualized by means of the FITC label (middle panel). FIG. 1 shows the results obtained for the 100 μM concentration of peptide F2, as a function of time. The labeled cell nuclei are shown on the left panels, the peptide F2 on the middle panels and the superimposition of these two labelings is represented on the right panels (panels marked fusion).

The peptide F2 according to the invention rapidly penetrates into the cells, and adopts a nuclear localization after only 30 minutes. In the absence of an additional intracellular targeting sequence, given the content rich in basic amino acids of the HIV-TAT penetration sequence, the latter also plays the role of NLS, and the peptide F2 is thereby advantageously localized in the nucleus.

The peptide F2 rapidly penetrates the cells and then adopts an exclusively nuclear localization.

Example 3

Example of Cell Penetration and of Cytoplasmic Localization of a Peptide According to the Invention The peptide F1 according to the invention ("docking peptide") is used here: it has the same sequence as the peptide P1 (see Example 1), and is coupled to FITC (fluorophore) at its C-terminal end.

It therefore has the following structure: [HIV-TAT penetrating peptide]-[C—C cleavage site]-[FXFP-type docking domain of the ERK/Elk-1 couple]-[FITC].

Figure 2:
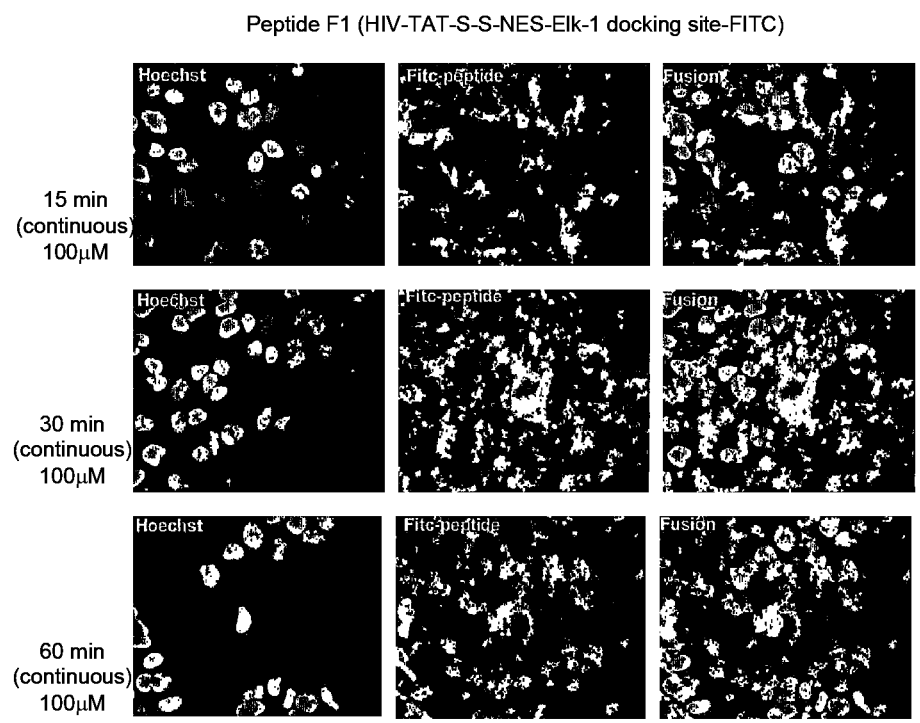
FIG. 2 shows results obtained for a 100 μM concentration of peptide F1, as a function of time.

HEK293 cells are placed in the presence of the peptide F1 at various concentrations (1 mM stock solution in distilled water, then dilutions to 25, 50 and 100 μM in DMEM culture medium) for 15, 30 or 60 minutes, continuously. The cell nuclei are labeled using Hoechst dye, and the peptide F1 is visualized by means of the FITC label. FIG. 2 shows the results obtained for the 100 μM concentration of peptide F1, as a function of time.

The labeled cell nuclei are shown on the left panels, the peptide F2 on the middle panels and the superimposition of these two labelings is represented on the right panels (panels marked fusion).

The peptide according to the invention rapidly penetrates the cells and adopts a cytoplasmic localization.

Example 4

Biochemical Characterization of the Inhibitory Effects of a Peptide According to the Invention: P2 Inhibits the Activation of Elk-1 by Serum in Mitotic Cells The peptide P2 according to the invention (see Example 1) is used here.

HEK cells were treated as indicated in Example 2 (FIG. 1) with the peptide P2 (40 minutes), followed by a treatment with serum (10%) for 20 minutes or 5 minutes. The serum activates the MAP kinase/ERK pathway.

Figure 3:
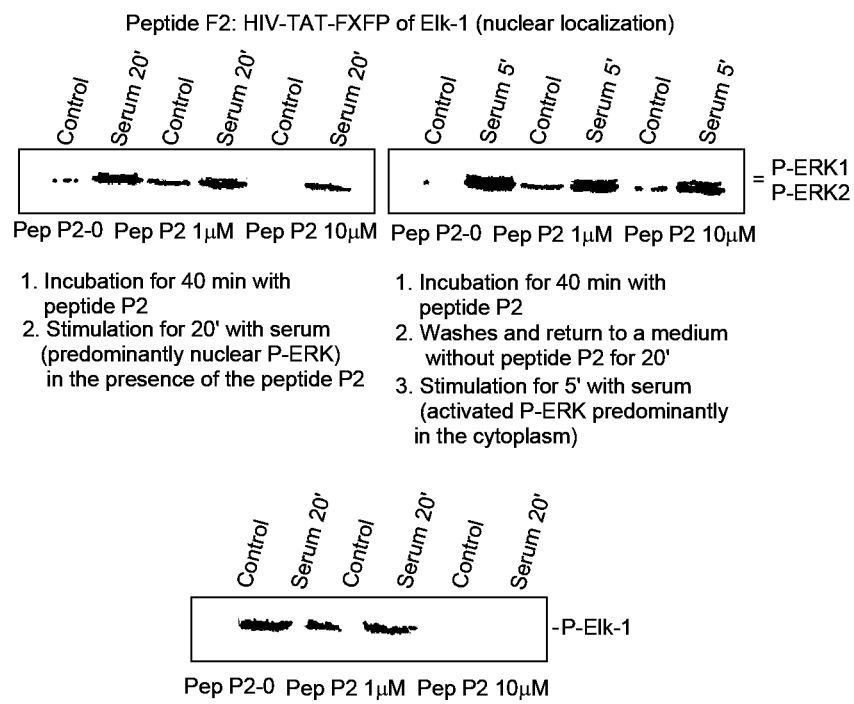
FIG. 3 is a chart depicting biochemical features of a peptide P2.

The activation of ERK is characterized by Western blotting using an anti-P-ERK1/2 antibody directed against the phosphorylated (active) form of ERK (anti rabbit Phospho Thr202-Tyr204 ERK, cell signaling, dilution 1/5000) (FIG. 3, top panels). The activation of Elk-1 is visualized with an anti-P-Elk-1 antibody directed against the phosphorylated form of Elk-1 (anti mouse Phospho Ser383 Elk-1, Santa-Cruz, dilution 1/200) (FIG. 3, bottom panel). The proteins are revealed using anti-rabbit and anti-mouse secondary antibodies respectively coupled to horseradish peroxidase (Amersham, dilutions 1/5000) and visualized by chemiluminescence (Amersham, ELC kit). Dose-response curves were produced in order to determine the lowest concentration of peptide which was effective.

Advantageously according to the invention, the induction of P-Elk-1 by serum is completely inhibited in the presence of the peptide P2 at 10 μM. This inhibition is absent at 1 μM of P2 (FIG. 3, bottom panel). The higher doses (50;100 μM) of peptide P2 are also found to be effective on the inhibition of Elk-1. Advantageously according to the invention, the induction of P-ERK by serum is not modified by the peptide P2 at 10 μM.

Example 5

Specificity of the Inhibition by a Peptide According to the Invention

The Phosphorylation of Elk-1 is Inhibited by P2, but not by P1

The peptides P1 and P2 according to the invention (see Example 1) are used here.

HEK cells are placed in the presence of the peptide P2 (FIG. 4, middle panels) or P1 (FIG. 4, right panels), at the concentration of 10 µM for 40 minutes. Nontreated cells (without peptide) are used as controls (FIG. 4, left panels).

The cells are then treated for 20 minutes using fetal calf serum (serum) in order to activate the MAP kinase/ERK pathway.

Figure 4:
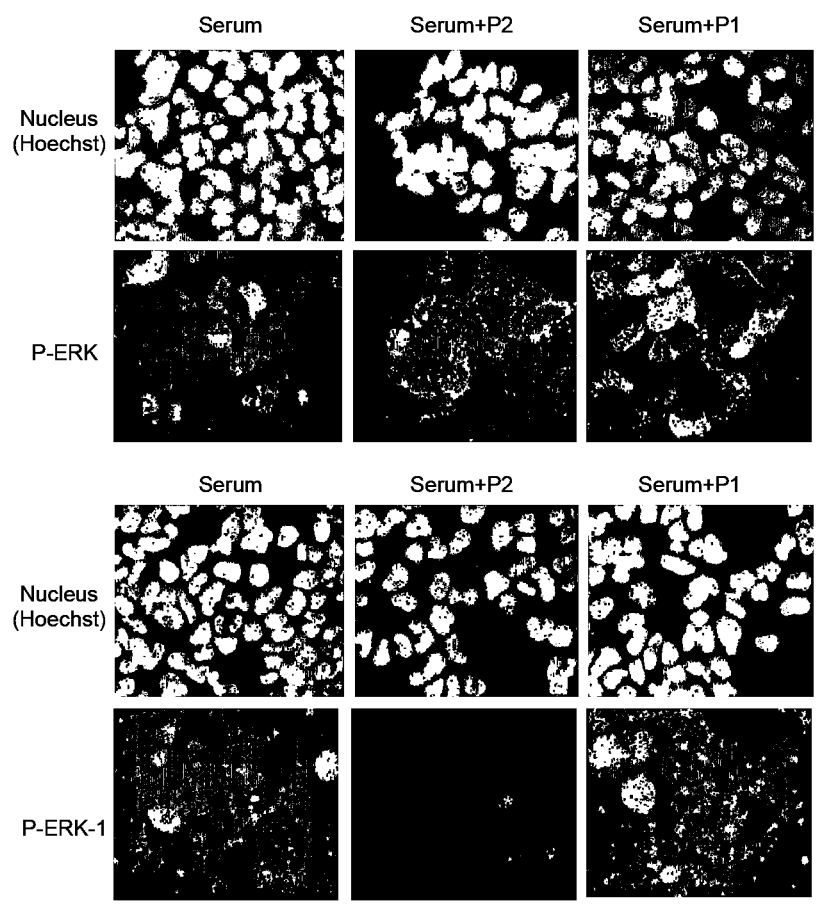
FIG. 4 shows results obtained for HEK cells placed in the presence of peptide P2, P1, or as non-treated cells.

The presence of the activated form of the ERK MAP kinase is visualized by immunodetection using an anti-phospho ERK antibody (anti rabbit Phospho Thr202-Tyr204 ERK, cell signaling, dilution 1/500 comment: the dilutions are indeed 10 times weaker for this experiment compared with the Western blotting) and revealed using a fluorescent secondary antibody coupled to Cy3 (anti rabbit Cy3, sigma, 1/2000) (FIG. 4, three panels of the second line marked P-ERK). The induction of P-ERK is clearly observed (FIG. 4, by way of example, a P-ERK labeling is represented by a white star, the nucleus of this cell is marked with the same star on the top panel corresponding to the Hoechst labeling), whatever the treatment conditions.

The presence of the activated form of Elk-1 is visualized by immunocytochemistry using an antibody against phospho-Ser383 of Elk-1 (anti mouse Phospho Ser383 Elk-1, Santa-Cruz, dilution 1/200) and revealed using an anti-mouse secondary antibody coupled to Cy3 (anti mouse Cy3, Jackson Immunoresearch, 1/600) (FIG. 4, by way of example, a P-Elk-1 labeling is represented by a white star, on the panels of the fourth line left and right). The corresponding nuclei are visualized by means of the same star on the panels of the third line, marked Hoechst.

The induction of P-Elk-1 is observed in the cytoplasmic and nuclear compartments in response to the serum (FIG. 4, panels of the fourth line on the left), and also in the presence of serum and of the peptide P1 (FIG. 4, panels of the fourth line on the right).

The absence of induction of P-Elk-1 is also observed in the cells pretreated with the peptide P2 (FIG. 4, panels of the fourth line in the middle).

Example 6

Biochemical Characterization of the Inhibitory Effects of a Peptide According to the Invention: P2 Inhibits the Activation of Elk-1 in Neurons in Response to an Excitatory Neurotransmitter, Glutamate Primary cultures of striatal neurons (taken at the E14 embryonic stage in mice) are cultured for 7 days in vitro in a neurobasal medium and then treated or not treated with the peptide P2 (5 µM) for one hour. The culture medium is subsequently renewed, and the neurons are then incubated for 30 minutes in a medium without peptide. An excitatory neurotransmitter, glutamate (100 µM), is then added, for 20 minutes, to the incubation wells marked Glu20'. The activation of ERK is characterized by Western blotting (FIG. 5A) using the anti-phospho ERK antibody as indicated in Example 4 (dilution: 1/5000).

Figure 5A:
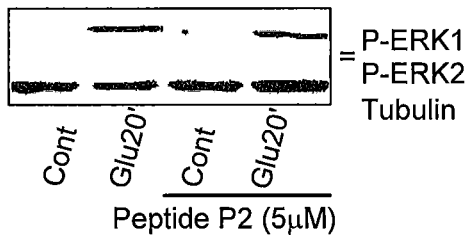
FIGS. 5A-5E depict biochemical effects of a peptide P2 on neurons in vitro.

Revelation of }-tubulin (monoclonal antibody, sigma, dilution 1/5000) on the same membrane makes it possible to have a loading control (FIG. 5A).

Figure 5C:
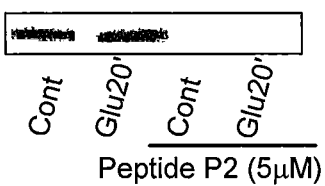
Figure 5D:
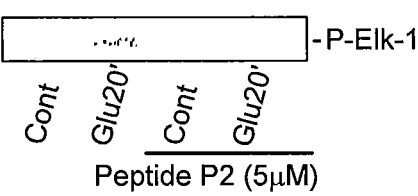
Figure 5B:
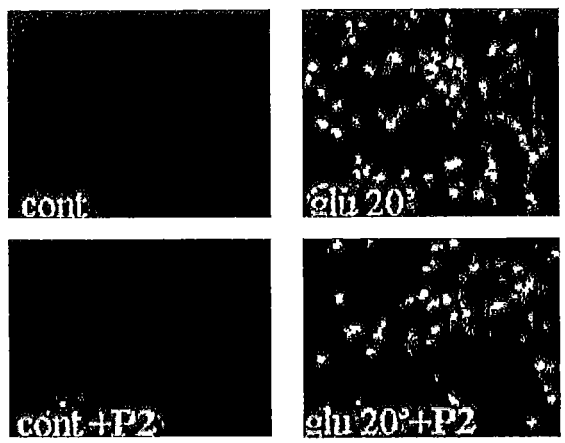

The P-ERK immunofluorescence (FIG. 5B) is carried out on neurons fixed with 2% paraformaldehyde, using the same antibody (dilution 1/500) revealed with a secondary antibody coupled to Cy3 (dilution 1/2000) (FIG. 5B). The peptide P2 does not block the activation of ERK, nor its nuclear translocation induced by glutamate in neurons.

Immunoprecipitations (FIG. 5C): neuronal extracts which are untreated or treated with the peptide P2 are immunoprecipitated using an anti-Elk-1 antibody (Santa-Cruz, 5 µl per immunoprecipitation). The ERK/Elk-1 interaction is revealed using these immunoprecipitated extracts, by Western blotting using an anti-ERK antibody (Santa-Cruz, dilution 1/5000) (FIG. 5C). The peptide P2 completely interferes with the ERK/Elk-1 interaction under the basal conditions and with glutamate treatment.

The activation of Elk-1 is visualized by Western blotting using an anti-phospho-Ser383-Elk-1 antibody as indicated in Example 4 by Western blotting (dilution 1/200) (FIG. 5D).

Figure 5E:
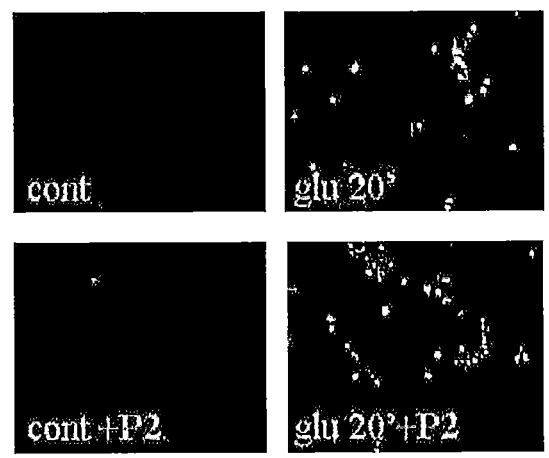

The activation of MSK1 is visualized by immunofluorescence using an anti-phospho-Thr581 MSK1 antibody (cell signaling, dilution 1/750) and revealed using a secondary antibody coupled to Cy3 (FIG. 5E).

The peptide P2 blocks the glutamate-induced activation of Elk-1 without impairing that of MSK1.

Example 7

Penetrability of the Peptide F2, In Vivo, in the Brain

Figure 6:
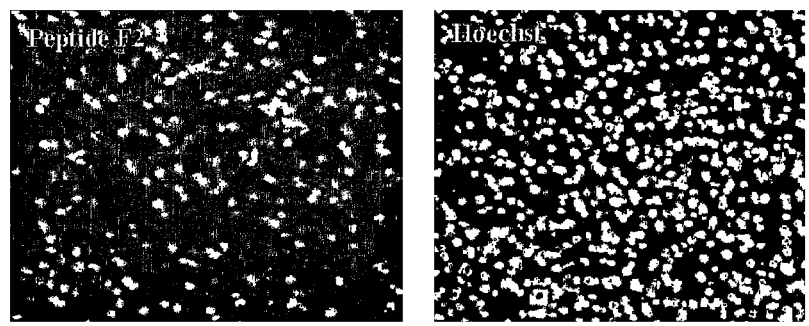
FIG. 6 shows the results of intracerebral injections of the peptide F2.

The peptide F2 (0.5 µl of 1 mM solution) according to the invention (see Example 1) is injected intracerebrally into the mouse striatum, using a microcannula. After injection, the microcannula remains in place for one hour. The mice are sacrificed by euthanasia by means of a lethal injection of pentobarbital, and then perfused intracardially with paraformaldehyde (4%). Thin sections (30 µm) are cut using a vibratome. The peptide F2 is visualized using a FITC filter (left panel), the nuclei are stained with Hoechst (middle panel). The penetrability of the peptide F2 in the majority of the cells should be noted (FIG. 6).

Example 8

Effect of the Peptide P2, In Vivo, in the Brain

Figure 7:
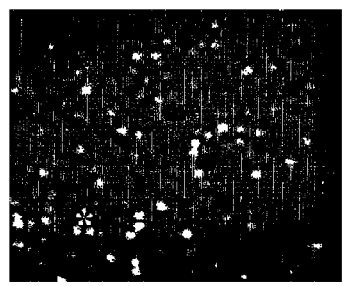
FIG. 7 shows the results of a peptide P2 on neurons in vivo.
Figure 7:
Figure 7:
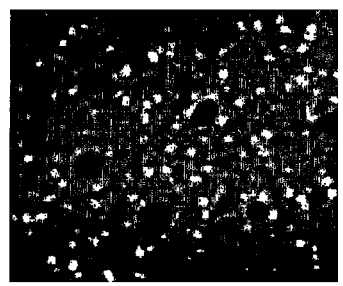
Figure 7:
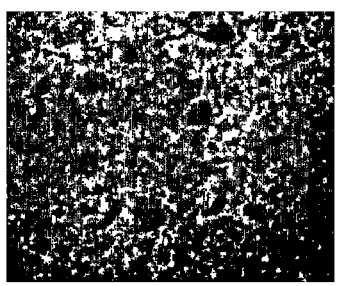

The peptide P2 (0.5 µl of a 1 mM solution) according to the invention (see Example 1) is injected intrastriatally as indicated in Example 7. In this case, a single hemisphere receives the peptide P2, the other hemisphere receives a saline solution. After one hour, cocaine (20 mg/kg) is administered intraperitoneally. The sacrifice by euthanasia, the intracardial perfusion and the sectioning of the brains are carried out, 10 minutes after the administration of cocaine, as indicated in Example 7. The activations of ERK and of Elk-1 induced in the striatum by the cocaine are visualized on the same section by double immunohistofluorescence, using the anti-phospho-ERK antibody mentioned in the previous examples (dilution 1/400) and a monoclonal anti-phospho-Elk-1 antibody (Santa Cruz, 1/100). The ERK activation is revealed with an anti-rabbit secondary antibody coupled to Cy3 (Amersham, 1/500), that of Elk-1 with an anti-mouse secondary antibody coupled to FITC (sigma, 1/100). It should be noted that the activation of ERK and Elk-1 takes place in the same cells in the absence of peptide (FIG. 7, top panel, white stars) and that, on the side which received the peptide P2, only the activation of ERK is detectable (FIG. 7, bottom panel).

What is claimed is:

1. A peptide comprising:
   at least one amino acid sequence which allows said peptide to penetrate into a cell, wherein one of the at least one amino acid sequences is SEQ ID No. 1;
   the amino acid sequence of SEQ ID No. 20 corresponding to a docking domain sequence of a substrate of an ERK-type MAP kinase;
   optionally, at least one spacer sequence;
   optionally, an enzymatic cleavage site;
   and optionally, a nuclear export signal (NES), wherein said docking domain sequence of a substrate of an ERK-type MAP kinase is a FXFP-type docking domain sequence, said peptide being a selective inhibitor of the activity of the ERK-type MAP kinase relative to the substrate.

2. A peptide according to claim 1, wherein the NES sequence which mediates the nuclear export of the peptide is chosen from SEQ ID No. 15, SEQ ID No. 16, SEQ ID No. 17, SEQ ID No. 18 and SEQ ID No. 19.

3. The peptide according to claim 1 wherein the spacer sequence is two prolines.

4. A peptide according to claim 1, wherein it comprises a NES sequence of SEQ ID No. 18 and the enzymatic cleavage site CC.

5. A nucleic acid encoding said peptide of claim 1.

6. An expression vector comprising said nucleic acid according to claim 5.

7. An expression vector according to claim 6 that is an eukaryotic expression vector.

* * * * *

```
                        SEQUENCE LISTING

<160> NUMBER OF SEQ ID NOS: 52

<210> SEQ ID NO 1
<211> LENGTH: 10
<212> TYPE: PRT
<213> ORGANISM: artificial
<220> FEATURE:
<223> OTHER INFORMATION: cell penetration sequence; nuclear localization
      signal sequence

<400> SEQUENCE: 1

Gly Arg Lys Lys Arg Arg Gln Arg Arg Arg
1               5                   10

<210> SEQ ID NO 2
<211> LENGTH: 16
<212> TYPE: PRT
<213> ORGANISM: artificial
<220> FEATURE:
<223> OTHER INFORMATION: cell penetration sequence; nuclear localization
      signal sequence

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 7
<212> TYPE: PRT
<213> ORGANISM: artificial
<220> FEATURE:
<223> OTHER INFORMATION: cell penetration sequence; nuclear localization
      signal sequence

<400> SEQUENCE: 3

Arg Arg Arg Arg Arg Arg Arg
1               5

<210> SEQ ID NO 4
<211> LENGTH: 9
<212> TYPE: PRT
<213> ORGANISM: artificial
<220> FEATURE:
<223> OTHER INFORMATION: cell penetration sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

Xaa Arg Arg Arg Arg Arg Arg Arg Xaa
1               5

<210> SEQ ID NO 5
<211> LENGTH: 9
<212> TYPE: PRT
<213> ORGANISM: artificial
<220> FEATURE:
<223> OTHER INFORMATION: cell penetration sequence
<220> FEATURE:
```

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 5

Xaa Arg Arg Arg Xaa Arg Arg Arg Arg
1               5

<210> SEQ ID NO 6
<211> LENGTH: 9
<212> TYPE: PRT
<213> ORGANISM: artificial
<220> FEATURE:
<223> OTHER INFORMATION: cell penetration sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 6

Arg Arg Arg Xaa Arg Arg Arg Arg Xaa
1               5

<210> SEQ ID NO 7
<211> LENGTH: 9
<212> TYPE: PRT
<213> ORGANISM: artificial
<220> FEATURE:
<223> OTHER INFORMATION: cell penetration sequence
<220> FEATURE:
<221> NAME/KEY: misc_feature
<222> LOCATION: (8)..(9)
<223> OTHER INFORMATION: Xaa can be any naturally occurring amino acid

<400> SEQUENCE: 7

Arg Arg Arg Arg Arg Arg Arg Xaa Xaa
1               5

<210> SEQ ID NO 8
<211> LENGTH: 9
<212> TYPE: PRT
<213> ORGANISM: artificial
<220> FEATURE:
<223> OTHER INFORMATION: cell penetration sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 8

Xaa Xaa Arg Arg Arg Arg Arg Arg Arg
1               5

<210> SEQ ID NO 9
<211> LENGTH: 11
<212> TYPE: PRT
<213> ORGANISM: artificial
<220> FEATURE:
<223> OTHER INFORMATION: cell penetration sequence; nuclear localization
      signal sequence

<400> SEQUENCE: 9
```

```
Arg Arg Arg Arg Arg Arg Arg Arg Arg Arg
1               5                   10
```

<210> SEQ ID NO 10
<211> LENGTH: 13
<212> TYPE: PRT
<213> ORGANISM: artificial
<220> FEATURE:
<223> OTHER INFORMATION: cell penetration sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 10

```
Xaa Arg Arg Arg Arg Arg Xaa Arg Arg Arg Arg Arg
1               5                   10
```

<210> SEQ ID NO 11
<211> LENGTH: 13
<212> TYPE: PRT
<213> ORGANISM: artificial
<220> FEATURE:
<223> OTHER INFORMATION: cell penetration sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 11

```
Arg Arg Arg Arg Arg Xaa Arg Arg Arg Arg Arg Xaa
1               5                   10
```

<210> SEQ ID NO 12
<211> LENGTH: 7
<212> TYPE: PRT
<213> ORGANISM: artificial
<220> FEATURE:
<223> OTHER INFORMATION: nuclear localization signal sequence

<400> SEQUENCE: 12

```
Pro Lys Lys Lys Arg Lys Val
1               5
```

<210> SEQ ID NO 13
<211> LENGTH: 16
<212> TYPE: PRT
<213> ORGANISM: artificial
<220> FEATURE:
<223> OTHER INFORMATION: nuclear localization signal sequence

<400> SEQUENCE: 13

```
Lys Arg Pro Ala Ala Ile Lys Lys Ala Gly Gln Ala Lys Lys Lys Lys
1               5                   10                  15
```

<210> SEQ ID NO 14
<211> LENGTH: 15
<212> TYPE: PRT
<213> ORGANISM: artificial
<220> FEATURE:
<223> OTHER INFORMATION: nuclear localization signal sequence

```
<400> SEQUENCE: 14

Arg Gln Ala Arg Arg Asn Arg Arg Asn Arg Arg Arg Arg Trp Arg
1               5                   10                  15

<210> SEQ ID NO 15
<211> LENGTH: 12
<212> TYPE: PRT
<213> ORGANISM: artificial
<220> FEATURE:
<223> OTHER INFORMATION: nuclear export signal sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 15

Xaa Leu Xaa Xaa Xaa Leu Xaa Xaa Leu Xaa Leu Xaa
1               5                   10

<210> SEQ ID NO 16
<211> LENGTH: 12
<212> TYPE: PRT
<213> ORGANISM: artificial
<220> FEATURE:
<223> OTHER INFORMATION: nuclear export signal sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 16

Xaa Leu Xaa Xaa Xaa Leu Xaa Xaa Leu Xaa Arg Xaa
1               5                   10

<210> SEQ ID NO 17
<211> LENGTH: 12
<212> TYPE: PRT
<213> ORGANISM: artificial
<220> FEATURE:
<223> OTHER INFORMATION: nuclear export signal sequence
```

```
<400> SEQUENCE: 17

Ala Leu Gln Lys Lys Leu Glu Glu Leu Glu Leu Asp
1               5                   10

<210> SEQ ID NO 18
<211> LENGTH: 12
<212> TYPE: PRT
<213> ORGANISM: artificial
<220> FEATURE:
<223> OTHER INFORMATION: nuclear export signal sequence

<400> SEQUENCE: 18

Thr Leu Trp Gln Phe Leu Leu Gln Leu Leu Leu Asp
1               5                   10

<210> SEQ ID NO 19
<211> LENGTH: 12
<212> TYPE: PRT
<213> ORGANISM: artificial
<220> FEATURE:
<223> OTHER INFORMATION: nuclear export signal sequence

<400> SEQUENCE: 19

Thr Leu Trp Gln Phe Leu Leu Gln Leu Leu Arg Glu
1               5                   10

<210> SEQ ID NO 20
<211> LENGTH: 18
<212> TYPE: PRT
<213> ORGANISM: artificial
<220> FEATURE:
<223> OTHER INFORMATION: FXFP-type docking domain sequence

<400> SEQUENCE: 20

Ser Pro Ala Lys Leu Ser Phe Gln Phe Pro Ser Gly Ser Ala Gln Val
1               5                   10                  15

His Ile

<210> SEQ ID NO 21
<211> LENGTH: 19
<212> TYPE: PRT
<213> ORGANISM: artificial
<220> FEATURE:
<223> OTHER INFORMATION: FXFP-type docking domain sequence

<400> SEQUENCE: 21

Ser Pro Ala Arg Leu Gln Gly Ala Asn Thr Leu Phe Gln Phe Pro Ser
1               5                   10                  15

Val Leu Asn

<210> SEQ ID NO 22
<211> LENGTH: 19
<212> TYPE: PRT
<213> ORGANISM: artificial
<220> FEATURE:
<223> OTHER INFORMATION: FXFP-type docking domain sequence

<400> SEQUENCE: 22

Ser Pro Ala Arg Leu Gln Gly Pro Ser Thr Leu Phe Gln Phe Pro Thr
1               5                   10                  15

Leu Leu Asn

<210> SEQ ID NO 23
<211> LENGTH: 18
```

```
<212> TYPE: PRT
<213> ORGANISM: artificial
<220> FEATURE:
<223> OTHER INFORMATION: FXFP-type docking domain sequence

<400> SEQUENCE: 23

Met Ala Val Leu Asp Arg Gly Thr Ser Thr Thr Thr Val Phe Asn Phe
1               5                   10                  15

Pro Val

<210> SEQ ID NO 24
<211> LENGTH: 16
<212> TYPE: PRT
<213> ORGANISM: artificial
<220> FEATURE:
<223> OTHER INFORMATION: FXFP-type docking domain sequence

<400> SEQUENCE: 24

Pro Asn Pro Ser Pro Gly Gln Arg Asp Ser Arg Phe Ser Phe Pro Asp
1               5                   10                  15

<210> SEQ ID NO 25
<211> LENGTH: 18
<212> TYPE: PRT
<213> ORGANISM: artificial
<220> FEATURE:
<223> OTHER INFORMATION: FXFP-type docking domain sequence

<400> SEQUENCE: 25

Ser Leu Thr Pro Thr Ala Ala His Ser Gly Ser His Leu Phe Gly Phe
1               5                   10                  15

Pro Pro

<210> SEQ ID NO 26
<211> LENGTH: 17
<212> TYPE: PRT
<213> ORGANISM: artificial
<220> FEATURE:
<223> OTHER INFORMATION: D-type docking domain sequence

<400> SEQUENCE: 26

Lys Gly Arg Lys Pro Arg Asp Leu Glu Leu Pro Leu Ser Pro Ser Leu
1               5                   10                  15

Leu

<210> SEQ ID NO 27
<211> LENGTH: 16
<212> TYPE: PRT
<213> ORGANISM: artificial
<220> FEATURE:
<223> OTHER INFORMATION: D-type docking domain sequence

<400> SEQUENCE: 27

Arg Ser Lys Lys Pro Lys Gly Leu Gly Leu Ala Pro Thr Leu Val Ile
1               5                   10                  15

<210> SEQ ID NO 28
<211> LENGTH: 18
<212> TYPE: PRT
<213> ORGANISM: artificial
<220> FEATURE:
<223> OTHER INFORMATION: D-type docking domain sequence

<400> SEQUENCE: 28

Lys Ala Lys Lys Pro Lys Gly Leu Glu Ile Ser Ala Pro Pro Leu Leu
```

<210> SEQ ID NO 29
<211> LENGTH: 17
<212> TYPE: PRT
<213> ORGANISM: artificial
<220> FEATURE:
<223> OTHER INFORMATION: D-type docking domain sequence

<400> SEQUENCE: 29

Ser Ser Ile Leu Ala Gln Arg Arg Val Arg Lys Leu Pro Ser Thr Thr
1               5                   10                  15

Leu

<210> SEQ ID NO 30
<211> LENGTH: 19
<212> TYPE: PRT
<213> ORGANISM: artificial
<220> FEATURE:
<223> OTHER INFORMATION: D-type docking domain sequence

<400> SEQUENCE: 30

Arg Arg Ser Thr Leu Ala Gln Arg Arg Gly Ile Lys Lys Ile Thr Ser
1               5                   10                  15

Thr Ala Leu

<210> SEQ ID NO 31
<211> LENGTH: 18
<212> TYPE: PRT
<213> ORGANISM: artificial
<220> FEATURE:
<223> OTHER INFORMATION: D-type docking domain sequence

<400> SEQUENCE: 31

Ser Ser Asn Leu Ala Gln Arg Arg Gly Met Lys Arg Leu Thr Ser Thr
1               5                   10                  15

Arg Leu

<210> SEQ ID NO 32
<211> LENGTH: 18
<212> TYPE: PRT
<213> ORGANISM: artificial
<220> FEATURE:
<223> OTHER INFORMATION: D-type docking domain sequence

<400> SEQUENCE: 32

Lys Ser Arg Leu Ala Arg Arg Arg Ala Leu Ala Gln Ala Gly Arg Ser
1               5                   10                  15

Arg Asp

<210> SEQ ID NO 33
<211> LENGTH: 19
<212> TYPE: PRT
<213> ORGANISM: artificial
<220> FEATURE:
<223> OTHER INFORMATION: D-type docking domain sequence

<400> SEQUENCE: 33

Gln Ser Lys Leu Ala Gln Arg Arg Gln Arg Ala Ser Leu Ser Ser Ala
1               5                   10                  15

Thr Pro Val

<210> SEQ ID NO 34
<211> LENGTH: 18
<212> TYPE: PRT
<213> ORGANISM: artificial
<220> FEATURE:
<223> OTHER INFORMATION: D-type docking domain sequence

<400> SEQUENCE: 34

Lys Ala Pro Leu Ala Lys Arg Arg Lys Met Lys Lys Thr Ser Thr Ser
1               5                   10                  15

Thr Glu

<210> SEQ ID NO 35
<211> LENGTH: 17
<212> TYPE: PRT
<213> ORGANISM: artificial
<220> FEATURE:
<223> OTHER INFORMATION: D-type docking domain sequence

<400> SEQUENCE: 35

Arg Phe Ser Thr Ile Val Arg Arg Ala Lys Gly Ala Lys Gly Ala
1               5                   10                  15

Gly

<210> SEQ ID NO 36
<211> LENGTH: 18
<212> TYPE: PRT
<213> ORGANISM: artificial
<220> FEATURE:
<223> OTHER INFORMATION: D-type docking domain sequence

<400> SEQUENCE: 36

Pro Gly Ile Met Leu Arg Arg Leu Gln Lys Gly Asn Leu Pro Val Arg
1               5                   10                  15

Ala Leu

<210> SEQ ID NO 37
<211> LENGTH: 17
<212> TYPE: PRT
<213> ORGANISM: artificial
<220> FEATURE:
<223> OTHER INFORMATION: D-type docking domain sequence

<400> SEQUENCE: 37

Leu Pro Ala Leu Leu Leu Arg Arg Leu Arg Arg Gly Ser Leu Ser Val
1               5                   10                  15

Arg

<210> SEQ ID NO 38
<211> LENGTH: 16
<212> TYPE: PRT
<213> ORGANISM: artificial
<220> FEATURE:
<223> OTHER INFORMATION: D-type docking domain sequence

<400> SEQUENCE: 38

Gly Leu Gln Glu Arg Arg Gly Ser Asn Val Ser Leu Thr Leu Asp Met
1               5                   10                  15

<210> SEQ ID NO 39
<211> LENGTH: 42
<212> TYPE: PRT
<213> ORGANISM: artificial
<220> FEATURE:

```
<223> OTHER INFORMATION: sequence which inhibits the interaction between
      Elk 1 and ERK

<400> SEQUENCE: 39

Gly Arg Lys Lys Arg Arg Gln Arg Arg Cys Cys Thr Leu Trp Gln
1               5                   10                  15

Phe Leu Leu His Leu Leu Leu Asp Ser Pro Ala Lys Leu Ser Phe Gln
            20                  25                  30

Phe Pro Ser Gly Ser Ala Gln Val His Ile
        35                  40

<210> SEQ ID NO 40
<211> LENGTH: 30
<212> TYPE: PRT
<213> ORGANISM: artificial
<220> FEATURE:
<223> OTHER INFORMATION: sequence which inhibits the interaction between
      Elk 1 and ERK

<400> SEQUENCE: 40

Gly Arg Lys Lys Arg Arg Gln Arg Arg Pro Pro Ser Pro Ala Lys
1               5                   10                  15

Leu Ser Phe Gln Phe Pro Ser Gly Ser Ala Gln Val His Ile
            20                  25                  30

<210> SEQ ID NO 41
<211> LENGTH: 42
<212> TYPE: PRT
<213> ORGANISM: artificial
<220> FEATURE:
<223> OTHER INFORMATION: sequence which inhibits the interaction between
      MKP 3 and ERK

<400> SEQUENCE: 41

Gly Arg Lys Lys Arg Arg Gln Arg Arg Cys Cys Thr Leu Trp Gln
1               5                   10                  15

Phe Leu Leu His Leu Leu Leu Asp Pro Gly Ile Met Leu Arg Arg Leu
            20                  25                  30

Gln Lys Gly Asn Leu Pro Val Arg Ala Leu
        35                  40

<210> SEQ ID NO 42
<211> LENGTH: 18
<212> TYPE: PRT
<213> ORGANISM: Artificial
<220> FEATURE:
<223> OTHER INFORMATION: FXFP-type docking domain sequence

<400> SEQUENCE: 42

Leu Val Thr Thr Thr Pro Thr Ser Thr Gln Phe Leu Tyr Pro Lys Val
1               5                   10                  15

Ala Ala

<210> SEQ ID NO 43
<211> LENGTH: 21
<212> TYPE: PRT
<213> ORGANISM: Artificial
<220> FEATURE:
<223> OTHER INFORMATION: FXFP-type docking domain sequence

<400> SEQUENCE: 43

Cys Thr Thr Tyr Thr Ser Ser Phe Val Phe Tyr Pro Glu Glu Ala
1               5                   10                  15
```

Asp Ser Phe Pro Ser
            20

<210> SEQ ID NO 44
<211> LENGTH: 20
<212> TYPE: PRT
<213> ORGANISM: Artificial
<220> FEATURE:
<223> OTHER INFORMATION: FXFP-type docking domain sequence

<400> SEQUENCE: 44

Ser Asn Gly Val Ile Thr Thr Thr Pro Thr Pro Gly Gln Tyr Phe
1               5                   10                  15

Tyr Pro Arg Gly
            20

<210> SEQ ID NO 45
<211> LENGTH: 17
<212> TYPE: PRT
<213> ORGANISM: Artificial
<220> FEATURE:
<223> OTHER INFORMATION: D-type docking domain sequence

<400> SEQUENCE: 45

Met Leu Lys Lys Asp Ala Leu Thr Leu Ser Leu Ala Glu Gln Gly Ala
1               5                   10                  15

Ala

<210> SEQ ID NO 46
<211> LENGTH: 20
<212> TYPE: PRT
<213> ORGANISM: Artificial
<220> FEATURE:
<223> OTHER INFORMATION: D-type docking domain sequence

<400> SEQUENCE: 46

Ser Gly Ala Ala Leu Cys Ala Leu Gly Lys Glu Cys Phe Leu Glu Leu
1               5                   10                  15

Ala Pro Asp Phe
            20

<210> SEQ ID NO 47
<211> LENGTH: 20
<212> TYPE: PRT
<213> ORGANISM: Artificial
<220> FEATURE:
<223> OTHER INFORMATION: D-type docking domain sequence

<400> SEQUENCE: 47

Asn Gly Gln Met Leu Cys Met Leu Gly Lys Glu Arg Phe Leu Glu Leu
1               5                   10                  15

Ala Pro Asp Phe
            20

<210> SEQ ID NO 48
<211> LENGTH: 22
<212> TYPE: PRT
<213> ORGANISM: Artificial
<220> FEATURE:
<223> OTHER INFORMATION: cell penetration sequence

<400> SEQUENCE: 48

Gly Ala Tyr Asp Leu Arg Arg Arg Glu Arg Gln Ser Arg Leu Arg Arg
1               5                   10                  15

-continued

```
Arg Glu Arg Gln Ser Arg
            20

<210> SEQ ID NO 49
<211> LENGTH: 14
<212> TYPE: PRT
<213> ORGANISM: Artificial
<220> FEATURE:
<223> OTHER INFORMATION: cell penetration sequence

<400> SEQUENCE: 49

Ser Arg Arg Ala Arg Arg Ser Pro Arg His Leu Gly Ser Gly
1               5                   10

<210> SEQ ID NO 50
<211> LENGTH: 16
<212> TYPE: PRT
<213> ORGANISM: Artificial
<220> FEATURE:
<223> OTHER INFORMATION: cell penetration sequence

<400> SEQUENCE: 50

Leu Arg Arg Glu Arg Gln Ser Arg Leu Arg Arg Glu Arg Gln Ser Arg
1               5                   10                  15

<210> SEQ ID NO 51
<211> LENGTH: 19
<212> TYPE: PRT
<213> ORGANISM: Artificial
<220> FEATURE:
<223> OTHER INFORMATION: cell penetration sequence

<400> SEQUENCE: 51

Val Lys Arg Gly Leu Lys Leu Arg His Val Arg Pro Arg Val Thr Arg
1               5                   10                  15

Met Asp Val

<210> SEQ ID NO 52
<211> LENGTH: 16
<212> TYPE: PRT
<213> ORGANISM: Artificial
<220> FEATURE:
<223> OTHER INFORMATION: cell penetration sequence

<400> SEQUENCE: 52

Arg Lys Lys Arg Arg Arg Glu Ser Arg Lys Lys Arg Arg Arg Glu Ser
1               5                   10                  15
```